United States Patent
Nair et al.

(10) Patent No.: US 12,176,107 B2
(45) Date of Patent: Dec. 24, 2024

(54) MODEL CHANGE MANAGEMENT OF ONLINE SOFTWARE AS A MEDICAL DEVICE

(71) Applicant: INTERNATIONAL BUSINESS MACHINES CORPORATION, Armonk, NY (US)

(72) Inventors: Rahul Nair, Mulhuddart (IE); Oznur Alkan, Mulhuddart (IE); Massimiliano Mattetti, Mulhuddart (IE); Elizabeth Daly, Mulhuddart (IE); Bei Chen, Mulhuddart (IE)

(73) Assignee: International Business Machines Corporation, Armonk, NY (US)

( * ) Notice: Subject to any disclaimer, the term of this patent is extended or adjusted under 35 U.S.C. 154(b) by 509 days.

(21) Appl. No.: 17/447,919

(22) Filed: Sep. 16, 2021

(65) Prior Publication Data
US 2023/0081085 A1     Mar. 16, 2023

(51) Int. Cl.
*G16H 50/20* (2018.01)
*G06F 18/00* (2023.01)
*G16H 50/30* (2018.01)

(52) U.S. Cl.
CPC ............. *G16H 50/20* (2018.01); *G06F 18/00* (2023.01); *G16H 50/30* (2018.01)

(58) Field of Classification Search
CPC ......... G16H 50/20; G16H 50/30; G06N 20/00
See application file for complete search history.

(56) References Cited

U.S. PATENT DOCUMENTS

| | | |
|---|---|---|
| 2002/0143276 A1 | 10/2002 | Ernst |
| 2005/0049910 A1 | 3/2005 | Lancaster et al. |
| 2006/0026304 A1* | 2/2006 | Price ................... G06F 8/65 710/62 |
| 2007/0180490 A1* | 8/2007 | Renzi ................. G06F 21/577 726/1 |
| 2012/0259652 A1 | 10/2012 | Mallon et al. |
| 2014/0018637 A1 | 1/2014 | Bennett |
| 2016/0125550 A1 | 5/2016 | Joao |
| 2016/0184497 A1 | 6/2016 | Phillips et al. |
| 2016/0371601 A1* | 12/2016 | Grove ................. G06N 20/00 706/12 |
| 2018/0232492 A1 | 8/2018 | Al-Alul et al. |

(Continued)

FOREIGN PATENT DOCUMENTS

| | | | |
|---|---|---|---|
| EP | 3629341 A1 | 4/2020 | |
| WO | WO2010132617 A2 * | 11/2010 | ............. G16H 10/60 |

OTHER PUBLICATIONS

Lee et al., Clinical applications of continual learning machine learning, 2(6) The Lancet Digital Health e279-e281 (Year: 2020).*

(Continued)

*Primary Examiner* — Jordan L Jackson
(74) *Attorney, Agent, or Firm* — Edward J. Wixted, III

(57) ABSTRACT

Machine learning model change management in an online Software as a Medical Device ("SaMD") is provided. One or more machine learning models implemented in a medical domain may be monitored where the one or more machine learning models are continuously updated. One or more changes to the one or more machine learning models. The one or more machine learning models, having the one or more changes, are certified as being in compliance with performance characteristics and compliance criteria.

17 Claims, 7 Drawing Sheets

(56) References Cited

U.S. PATENT DOCUMENTS

| | | | |
|---|---|---|---|
| 2018/0360295 | A1 | 12/2018 | Boucher |
| 2020/0234816 | A1 | 7/2020 | De Armas |
| 2020/0234817 | A1 | 7/2020 | De Armas |
| 2020/0285568 | A1* | 9/2020 | Alff ............... G06F 11/3684 717/104 |
| 2020/0320349 | A1* | 10/2020 | Yu .................. H04L 9/3239 706/12 |
| 2021/0295427 | A1* | 9/2021 | Shiu ............... G06Q 40/03 705/38 |

OTHER PUBLICATIONS

Vartak et al., ModelDB: a system for machine learning model management, HILDA '16: Proceedings of the Workshop on Human-In-the-Loop Data Analytics (Jun. 26, 2016) (Year: 2016).*

De Lange et al., A Continual Learning Survey: Defying Forgetting in Classification Tasks, 44(7) IEEE Transactions on Pattern Analysis and Machine Intelligence 3366-3385 (Feb. 5, 2021) (Year: 2021).*

Author Unknown, "Scalable eQMS software to make quality easy", https://www.qualio.com/, Qualio, #1 Cloud-based Quality Management Software for MedDevice & Pharma, Accessed Feb. 12, 2024, pp. 1-13.

Benjamens, et. al., "The state of artificial intelligence-based FDA-approved medical devices and algorithms: an online database", https://www.nature.com/articles/s41746-020-00324-0#Fig1, npj Digital Medicine, 3 article No. 118, Sep. 11, 2020, pp. 1-8.

Clarke, et al., "MDevSPICE—A Comprehensive Solution for Manufacturers and Assessors of Safety-Critical Medical Device Software", SPICE 2014, CCIS 477, pp. 274-278, 2014, © Springer International Publishing Switzerland 2014, pp. 274-278.

Feng, et. al., "Approval policies for modifications to Machine Learning-Based Software as a Medical Device: A study of bio-creep", https://arxiv.org/pdf/1912.12413.pdf, arXiv:1912.12413v1 [stat.ML] Dec. 28, 2019, pp. 1-14.

Fenton, "What to Consider When Choosing Quality Management Software (eQMS) for Medical Devices [8 Factors]", https://www.qualio.com/blog/quality-management-software-for-medical-devices, Qualio, Medical Devices, Jan. 16, 2020, Accessed Feb. 12, 2024, pp. 1-12.

Minhas, et al., "UML Profiling for Software Systems in Medical Device Manufacturing", https://link.springer.com/chapter/10.1007/978-3-030-28957-7_22, © Springer Nature Switzerland AG 2019, K. Saeed et al. (Eds.): CISIM 2019, LNCS 11703, pp. 265-277.

Morrison, et al., "Advancing Regulatory Science With Computational Modeling for Medical Devices at the FDA's Office of Science and Engineering Laboratories", https://www.ncbi.nlm.nih.gov/pmc/articles/PMC6167449/, Frontiers in Medicine, Sep. 2018, vol. 5, Article 241, pp. 1-11.

Panigutti, et al., "FairLens: Auditing Black-box Clinical Decision Support Systems", https://arxiv.org/abs/2011.04049, arXiv, Computer Science > Machine Learning, Nov. 8, 2020, accessed Feb. 12, 2024, pp. 1-17.

* cited by examiner

MODEL CHANGE MANAGEMENT OF ONLINE SOFTWARE AS A MEDICAL DEVICE

BACKGROUND

The present invention relates in general to computing systems, and more particularly, to various embodiments for providing machine learning model change management in an online Software as a Medical Device ("SaMD") in a computing systems using a computing processor.

SUMMARY

According to an embodiment of the present invention, a method for providing machine learning model change management in of an online Software as a Medical Device ("SaMD") in a computing environment, by one or more processors, is depicted. One or more machine learning models implemented in a medical domain may be monitored where the one or more machine learning models are continuously updated. One or more changes to the one or more machine learning models. The one or more machine learning models, having the one or more changes, are certified as being in compliance with performance characteristics and compliance criteria.

An embodiment includes a computer usable program product. The computer usable program product includes a computer-readable storage device, and program instructions stored on the storage device.

An embodiment includes a computer system. The computer system includes a processor, a computer-readable memory, and a computer-readable storage device, and program instructions stored on the storage device for execution by the processor via the memory.

Thus, in addition to the foregoing exemplary method embodiments, other exemplary system and computer product embodiments are provided.

DETAILED DESCRIPTION OF THE DRAWINGS

Figure 1:
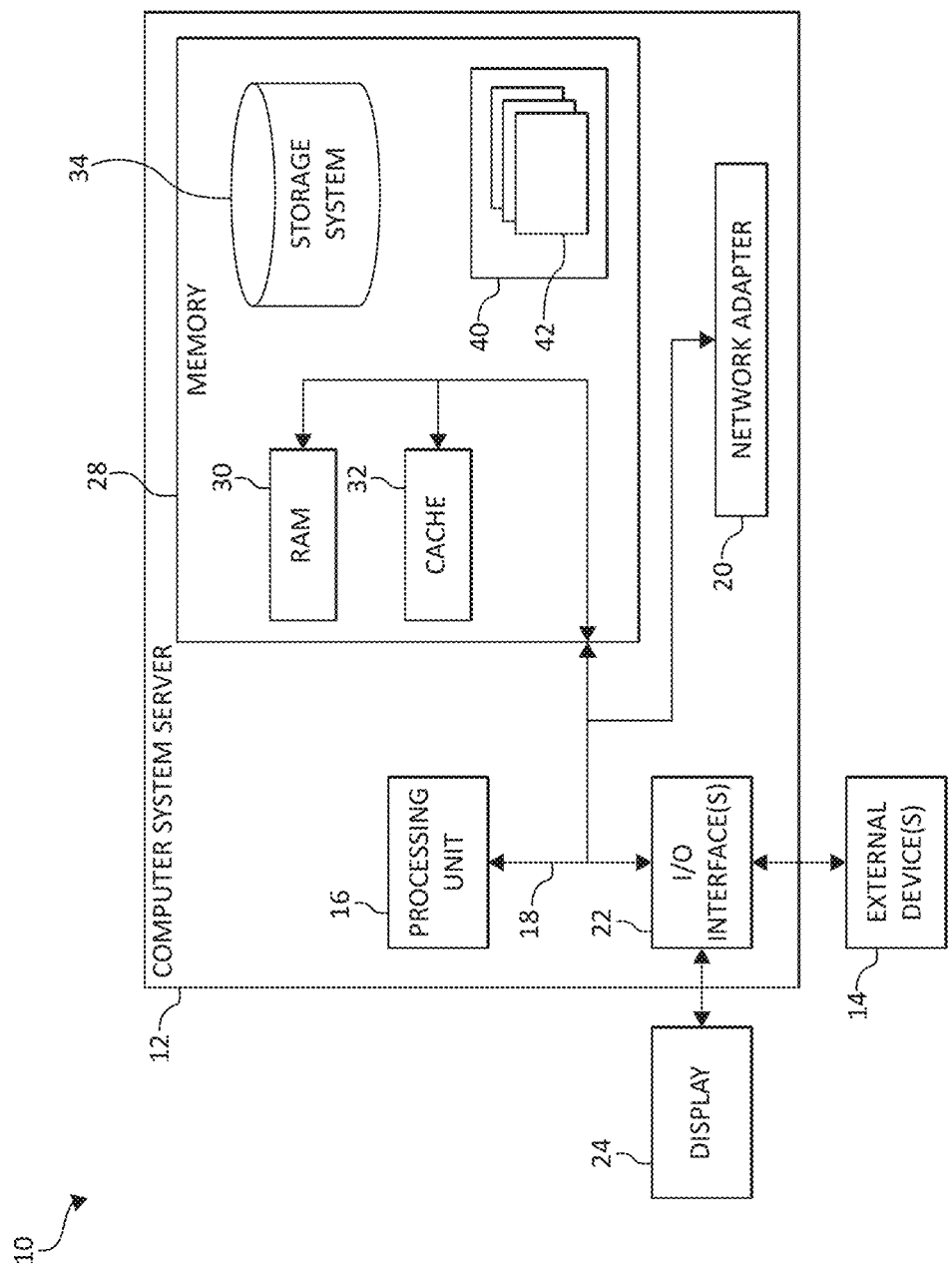
FIG. 1 is a block diagram depicting an exemplary cloud computing node according to an embodiment of the present invention.

In today's society, consumers, businesspersons, educators, and others communicate over a wide variety of mediums in real time, across great distances, and many times without boundaries or borders. The advent of computers and networking technologies have made possible the increase in the quality of life while enhancing day-to-day activities.

Computing systems may be found in the workplace, at home, or at school. Due to the recent advancement of information technology and the growing popularity of the Internet, a wide variety of computer systems have been used in machine learning. For example, Artificial intelligence (AI) and machine learning (ML) technologies provides critical assistance within the health care profession by generating new and important insights from the large amount of data generated during the delivery of health care every day. Medical device manufacturers use these technologies to innovate their products to better assist health care providers and improve patient care.

AI/ML in software within the medical domain is the ability to learn from real-world use and experience, and its capability to improve its performance. For example, the United States Food and Drug Administration ("FDA") refers to software functions that are device functions as "device software functions" or "Software as a Medical Device (SaMD)" and "Software in a Medical Device (SiMD). That is, these AI/ML, systems used in medical settings are classed as "Software as a Medical Device" (SaMD) by regulators. Thus, in one aspect, as used herein, a SaMD may collect, process, diagnose, and analyze health care data to improve health, accelerate treatment, diagnose disease, or monitor various health care data. Moreover, the FDA further distinguishes AI/ML models as being either "locked" (e.g., unchanged), and "online" (e.g., those SaMD's that dynamically learn, retrain, and adapt based on new data).

Vendors of such AI/ML systems must seek pre-approval (e.g., regulatory approval) for any modifications to their system, if there are any changes in performance, inputs/outputs, or intended use. These regulators have several approval pathways for such systems and have a risk classification system.

As used herein, the term SaMD may be defined as software intended to be used for one or more medical purposes that perform these purposes without being part of a hardware medical device. Medical device may mean any instrument, apparatus, implement, machine, appliance, implant, reagent for in vitro use, software, material or other similar or related article, intended by the manufacturer to be used, alone or in combination, for human beings, for one or more of the specific medical purpose(s) such as, for example, diagnosis, prevention, monitoring, treatment, alleviation of disease, injury, physiological process, compensation for an injury, investigation, replacement, modification, or support of the anatomy or of a physiological process, supporting or sustaining health and life. Thus, a medical device may be any device used in the medical domain.

While machine model retraining can be automatic, several operations in retraining a machine model are not automatic. Thus, the present invention provides for automatically providing machine learning model change management in an online Software as a Medical Device ("SaMD") in a computing environment. One or more machine learning models implemented in a medical domain may be monitored where the one or more machine learning models are continuously updated. One or more changes may be made to the one or more machine learning models. The one or more machine learning models, having the one or more changes, are certified as being in compliance with performance characteristics and compliance criteria.

The present invention provides for automatically assessing changes to clinical or analytical performance (e.g., improved specificity of method in detecting abnormal tissue in a scan) is not automatic, determining the impact of a change in disparate across various demographic groups, data signals in the model impact analytical performance. Also, embodiments of the present invention provide for operations such as, for example, determining the impact of the change disparate across various demographic groups, determining whether new data signals in the model impact analytical performance, determining if model updates involve a change to the scope of use, and if so, determining whether these changes require a re-certification of the product.

In an additional aspect, the present disclosure provides an AI/ML model management function for online AI models such as, for example, the ability to describe (e.g., in plain text or interpretable data) clinical context for an online AI/ML model. In an additional aspect, the present disclosure provides the ability to update/retrain model and trigger model validation (both clinical and analytical). In an additional aspect, the present disclosure provides the ability to configure the model (e.g., data selection, model tuning, and/or other features).

In one aspect, the present disclosure provides for model comparison functions such as, for example, the ability to compare a newly trained model with previous model and compare and contrast performance measures between AI/ML model versions.

In an additional aspect, the present disclosure provides for the ability to provide a human interpretable summary of changes, manage regulatory implications of AI/ML model changes (e.g., functionality to determine if changes have a material impact on compliance, and functions) to determine if changes may require re-certification of product. In another aspect, the present disclosure provides for an alerting component or signal to a vendor if an online/adaptable model has undergone substantial change. Thus, the AI/ML model may learn, collect, monitor, manage, store, and/or update input and training data.

As used herein, a user may be defined as, for example, a human (e.g., patient, expert, a care coordinator, nurses, doctors, counselors, etc.), vendor, manufacturer, a client and/or customer of a business (either an entity or human), and/or an entity/person that has previously interacted with one or more components of the present invention. The user may be an entity/person interacting with the present invention as described herein. Input data may include a health state of a user, historical medical data, patient/user profile and history, similarity of the patient/user with other (anonymized) client profiles, history of interactions with other (anonymized) patient/user, activities of daily living ("ADLs"), goals (formulated as text) defined by one or more domain experts.

In one aspect, the health state (e.g., wellness) may include at least one or more medical conditions of one or more clients, a health state (e.g., subjective health state "SWB", emotional health state, mental health state, physical health state, or an overall health state) of the one or more clients, an emotional state of the one or more clients, biometric data, behavior patterns, a health profile of the client, or a combination thereof. In one aspect, health state may be generally described as a normal/standardized or satisfactory condition of existence of the client, or a state characterized by health, happiness, emotional stability, mental stability, physical stability, or success. As one of ordinary skill in the art will appreciate, "health state" may be dependent on a number of factors, including such factors as medical condition, emotional stability, mental stability, physical stability, financial stability, a degree or level of happiness, or other factors that may be learned. A health state of a client/patient may be defined. For example, a knowledge base or ontology may be used to define a health state for a client/patient and may include defining and/or indicating one or more correlations between a health state, a plurality of states, medical conditions, activities of daily living (ADL), and context of daily living (CDL).

Moreover, as used herein, ADLs may refer to the most common activities that people perform during a day. For example, activities of daily living may include many activities that take place throughout the day, particularly going to work, child-care, elderly care, health management, communication management, financial management, safety/emergency responses, shopping, visiting friends or family, traveling, housekeeping, grooming or personal hygiene practices, meal preparation/dining out, engaging in social media, and even using a computer. ADLs may also be used in terms of healthcare to refer to the person's daily self-care activities. The context of daily living ("CDL" or "CDLs") may refer to the context in which one or more ADLs are executed or carried out. The CDL may also include one or more dimensions such as, for example, time, location, environment conditions, weather conditions, traffic conditions, and the like. A domain knowledge may provide one or more correlations or relationships between a person's health state and the ADLs and CDLs.

Some ADLs may also be applicable for one or more types of specific events. For example, a person having experienced a recent surgical procedure may require different or altered ADLs for treatment, recovery, or even resuming previously enjoyed ADLs. Each organism (e.g., person) may have different ADLs than other persons. Accordingly, the ADLs for each person may be learned, identified, and analyzed as part of the machine learning models implemented in a medical device. In one aspect, the ADLs for a person may be learned such as, for example, using machine learning or using a domain knowledge relating to information about the person's activities and behaviors, which may be stored in a patient profile.

It should be noted as used herein, "intelligent" (or "intelligence") may refer to a mental action or process of acquiring knowledge and understanding through thought, experience, and one or more senses using machine learning (which may include using sensor-based devices or other computing systems that include audio or video devices). "Intelligence" may also refer to identifying patterns of behavior, leading to a "learning" of one or more events, operations, or processes. The term "intelligent" or "intelligence" may refer to an artificial intelligent/machine learning system. The intelligent system may be a specialized computer system, or set of computer systems, configured with hardware and/or software logic (in combination with hardware logic upon which the software executes) to emulate human cognitive functions. These intelligent systems apply human-like characteristics to convey and manipulate ideas which, when combined with the inherent strengths of digital computing, can solve problems with a high degree of accuracy (e.g., within a defined percentage range or above an accuracy threshold) and resilience on a large scale. An intelligent system may perform one or more computer-implemented cognitive operations that approximate a human thought process while enabling a user or a computing system to interact in a more natural manner. An intelligent system may comprise artificial intelligence logic, such as natural language processing (NLP) based logic, for example, and machine learning logic, which may be provided as specialized hardware, software executed on hardware, or any combination of specialized hardware and software executed on hardware. The logic of the intelligent system may implement the cognitive operation(s), examples of which include, but are not limited to, question answering, identification of related concepts within different portions of content in a corpus, and intelligent search algorithms, such as Internet web page searches.

In general, such intelligent systems are able to perform the following functions: 1) Navigate the complexities of human language and understanding; 2) Ingest and process vast amounts of structured and unstructured data; 3) Generate and evaluate hypotheses; 4) Weigh and evaluate responses that are based only on relevant evidence; 5) Provide situation-specific advice, insights, estimations, determinations, evaluations, calculations, and guidance; 6) Improve knowledge and learn with each iteration and interaction through machine learning processes; 7) Enable decision making at the point of impact (contextual guidance); 8) Scale in proportion to a task, process, or operation; 9) Extend and magnify human expertise and cognition; 10) Identify resonating, human-like attributes and traits from natural language; 11) Deduce various language specific or agnostic attributes from natural language; 12) Memorize and recall relevant data points (images, text, voice) (e.g., a high degree of relevant recollection from data points (images, text, voice) (memorization and recall)); and/or 13) Predict and sense with situational awareness operations that mimic human cognition based on experiences.

It should be noted that one or more calculations may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

In general, such cognitive systems are able to perform the following functions: 1) Navigate the complexities of human language and understanding; 2) Ingest and process vast amounts of structured and unstructured data; 3) Generate and evaluate hypotheses; 4) Weigh and evaluate responses that are based only on relevant evidence; 5) Provide situation-specific advice, insights, estimations, determinations, evaluations, calculations, and guidance; 6) Improve knowledge and learn with each iteration and interaction through machine learning processes; 7) Enable decision making at the point of impact (contextual guidance); 8) Scale in proportion to a task, process, or operation; 9) Extend and magnify human expertise and cognition; 10) Identify resonating, human-like attributes and traits from natural language; 11) Deduce various language specific or agnostic attributes from natural language; 12) Memorize and recall relevant data points (images, text, voice) (e.g., a high degree of relevant recollection from data points (images, text, voice) (memorization and recall)); and/or 13) Predict and sense with situational awareness operations that mimic human cognition based on experiences.

It should be noted that a cognitive system may also perform one or more calculations that may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

In general, as used herein, "optimize" may refer to and/or defined as "maximize," "minimize," "best," or attain one or more specific targets, objectives, goals, or intentions. Optimize may also refer to maximizing a benefit to a user (e.g., maximize a trained machine learning scheduling agent benefit). Optimize may also refer to making the most effective or functional use of a situation, opportunity, or resource.

Additionally, optimizing need not refer to a best solution or result but may refer to a solution or result that "is good enough" for a particular application, for example. In some implementations, an objective is to suggest a "best" combination of operations, schedules, PE's, and/or machine learning models/machine learning pipelines, but there may be a variety of factors that may result in alternate suggestion of a combination of operations, schedules, PE's, and/or machine learning models/machine learning pipelines yielding better results. Herein, the term "optimize" may refer to such results based on minima (or maxima, depending on what parameters are considered in the optimization problem). In an additional aspect, the terms "optimize" and/or "optimizing" may refer to an operation performed in order to achieve an improved result such as reduced execution costs or increased resource utilization, whether or not the optimum result is actually achieved. Similarly, the term "optimize" may refer to a component for performing such an improvement operation, and the term "optimized" may be used to describe the result of such an improvement operation.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random-access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD- ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
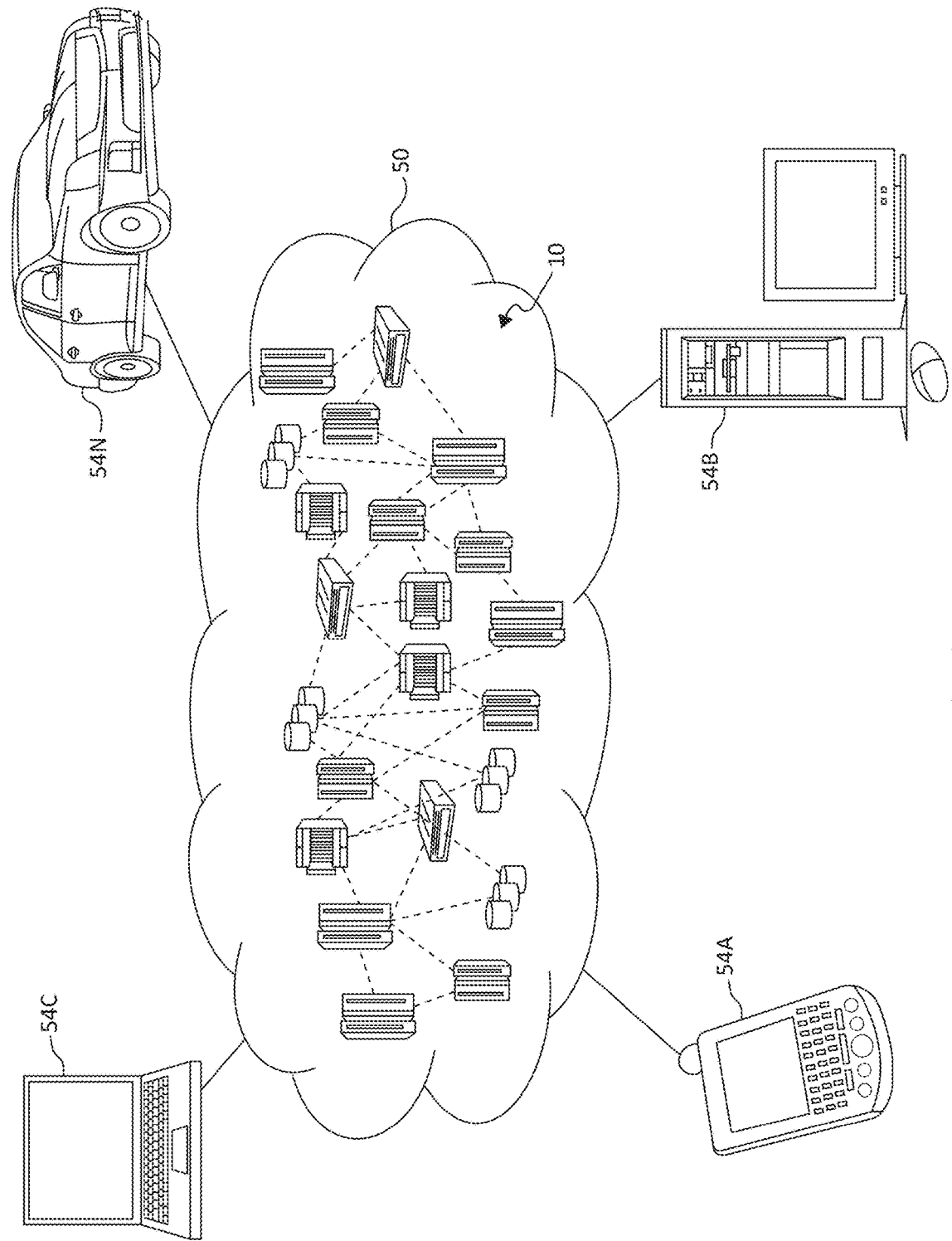
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
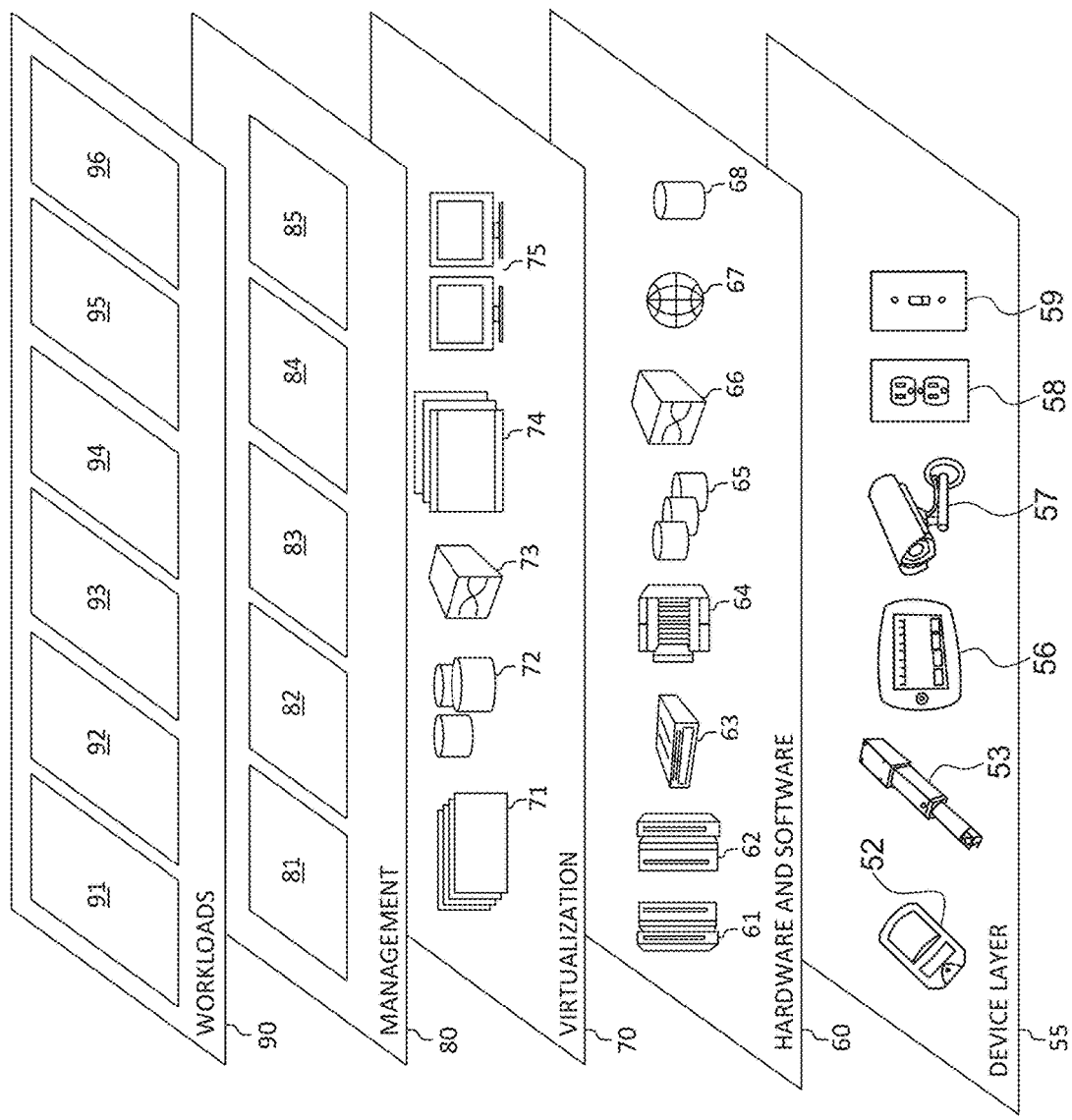
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various workloads and functions 96 for dynamic task scheduling in heterogenous systems using a machine learning agent in a computing environment (e.g., in a neural network architecture). In addition, workloads and functions 96 for dynamic task scheduling in heterogenous systems using a machine learning agent in a computing environment may include such operations as analytics, deep learning, and as will be further described, user and device management functions. One of ordinary skill in the art will appreciate that the workloads and functions 96 for dynamic task scheduling in heterogenous systems using a machine learning agent in a computing environment may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

As previously stated, the present invention provides novel solutions for providing online AI/ML models that provide the ability to describe clinical context for an online AI/ML model. The online AI/ML model may update/retrain the model and trigger model validation (both clinical and analytical). The online AI/ML model may configure an online machine learning model (e.g., configure data selection, model tuning, and any new features or parameters). The online AI/ML model may provide a model comparison functions, i.e., the ability to compare a newly trained model with previous AI/ML model. The online AI/ML model may compare and contrast performance measures between model versions. The online AI/ML model may provide the ability to provide a user-interpretable (e.g., understandable by a human) summary of changes. The online AI/ML model may manage regulatory implications of AI model changes, i.e., functionality to determine if changes have a material impact on compliance, operations to determine if changes may require re-certification of product, alternations to vendor if an online/adaptable model has undergone substantial change.

Figure 4:
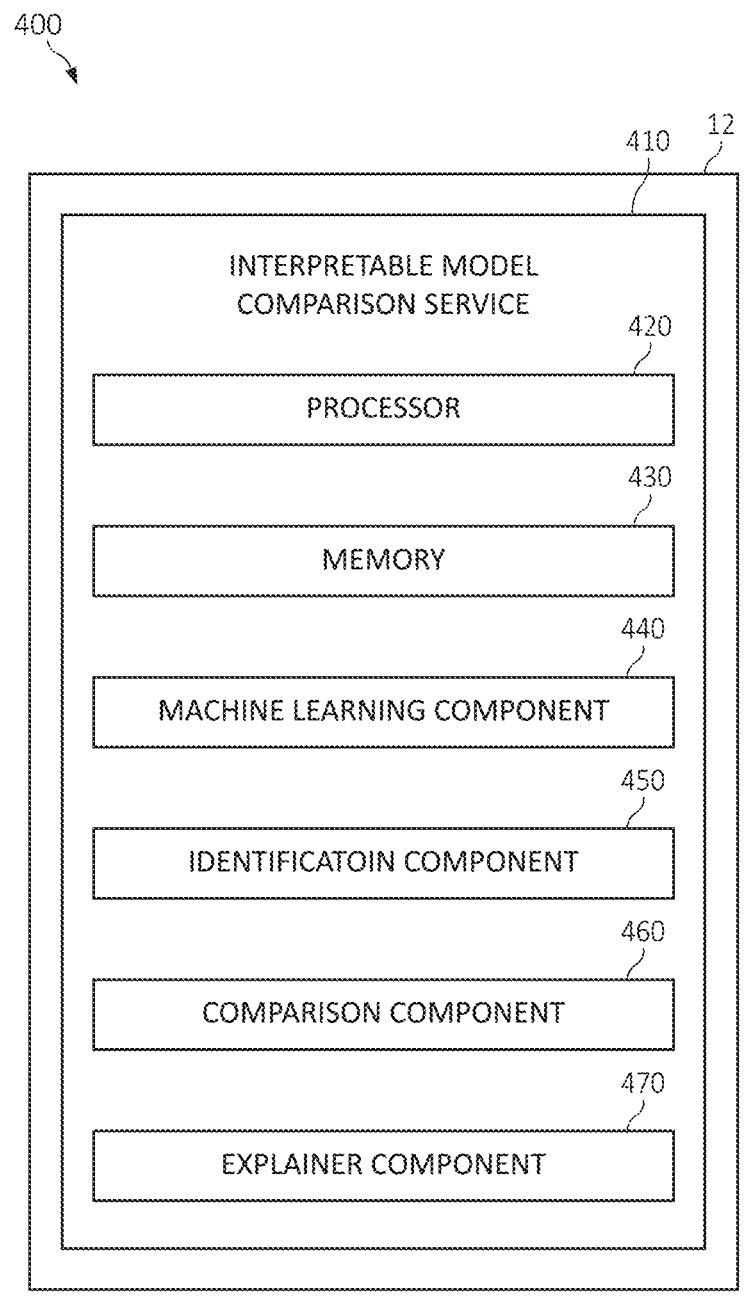
FIG. 4 is an additional block diagram depicting an exemplary functional relationship between various aspects of the present invention.

Turning now to FIG. 4, a block diagram depicting exemplary functional components of system 400 for providing machine learning model change management in of an online Software as a Medical Device ("SaMD") in a computing environment according to various mechanisms of the illustrated embodiments is shown. In one aspect, one or more of the components, modules, services, applications, and/or functions described in FIGS. 1-3 may be used in FIG. 4. As will be seen, many of the functional blocks may also be considered "modules" or "components" of functionality, in the same descriptive sense as has been previously described in FIGS. 1-3.

An interpretable model comparison service 410 is shown, incorporating processing unit 420 ("processor") to perform various computational, data processing and other functionality in accordance with various aspects of the present invention. In one aspect, the processor 420 and memory 430 may be internal and/or external to the interpretable model comparison service 410, and internal and/or external to the computing system/server 12. The interpretable model comparison service 410 may be included and/or external to the computer system/server 12, as described in FIG. 1. The processing unit 420 may be in communication with the memory 430. The interpretable model comparison service 410 may include a machine learning component 440, an identification component 450, a comparison component 460, and an explainer component 470.

In one aspect, the system 400 may provide virtualized computing services (i.e., virtualized computing, virtualized storage, virtualized networking, etc.). More specifically, the system 400 may provide virtualized computing, virtualized storage, virtualized networking and other virtualized services that are executing on a hardware substrate.

The interpretable model comparison service 410 may, using the machine learning component 440, the identification component 450, the comparison component 460, and the explainer component 470, monitor one or more machine learning models implemented in a medical domain, wherein the one or more machine learning models are continuously updated; identify one or more changes to the one or more machine learning models; and certify the one or more machine learning models having the one or more changes are in compliance with performance characteristics and compliance criteria.

Also, the interpretable model comparison service 410 may, using the machine learning component 440, the identification component 450, the comparison component 460, and the explainer component 470 may track model versions, provenance, clinical context, and performance of a medical device. It should be noted that "provenance" may refer to or imply an origin of a specific model such as, for example, information about that original training data of the model, the original version of the algorithm used to train the model, and all original training parameters of the model.

The comparison component 460, in association with the explainer component 470, may provide an interpretable model comparison between a current more machine learning model and an updated machine learning model.

The identification component 460 may track each version of the one or more machine learning models in the medical domain. The identification component 450 may identify the one or more changes compromise the performance characteristics and compliance criteria of the one or more machine learning models.

The comparison component 460, in association with the explainer component 470, may update and retain the one or more machine learning models to achieve compliance with the performance characteristics and compliance criteria.

The comparison component 460, in association with the explainer component 470, may map the one or more changes of the one or more machine learning models to a risk assessment domain.

The interpretable model comparison service 410 may, using the machine learning component 440, the identification component 450, the comparison component 460, and the explainer component 470 may build an interpretable rule set based on performance characteristics and compliance criteria, validate the one or more machine learning models against the interpretable rule set; and generate a certificate indicating the one or more machine learning models comply with interpretable rule set.

In one aspect, the machine learning component 440 as described herein, may perform various machine learning operations using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, backpropagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are within the scope of this disclosure. Also, when deploying one or more machine learning models, a computing device may be first tested in a controlled environment before being deployed in a public setting. Also even when deployed in a public environment (e.g., external to the controlled, testing environment), the computing devices may be monitored for compliance.

Figure 5:
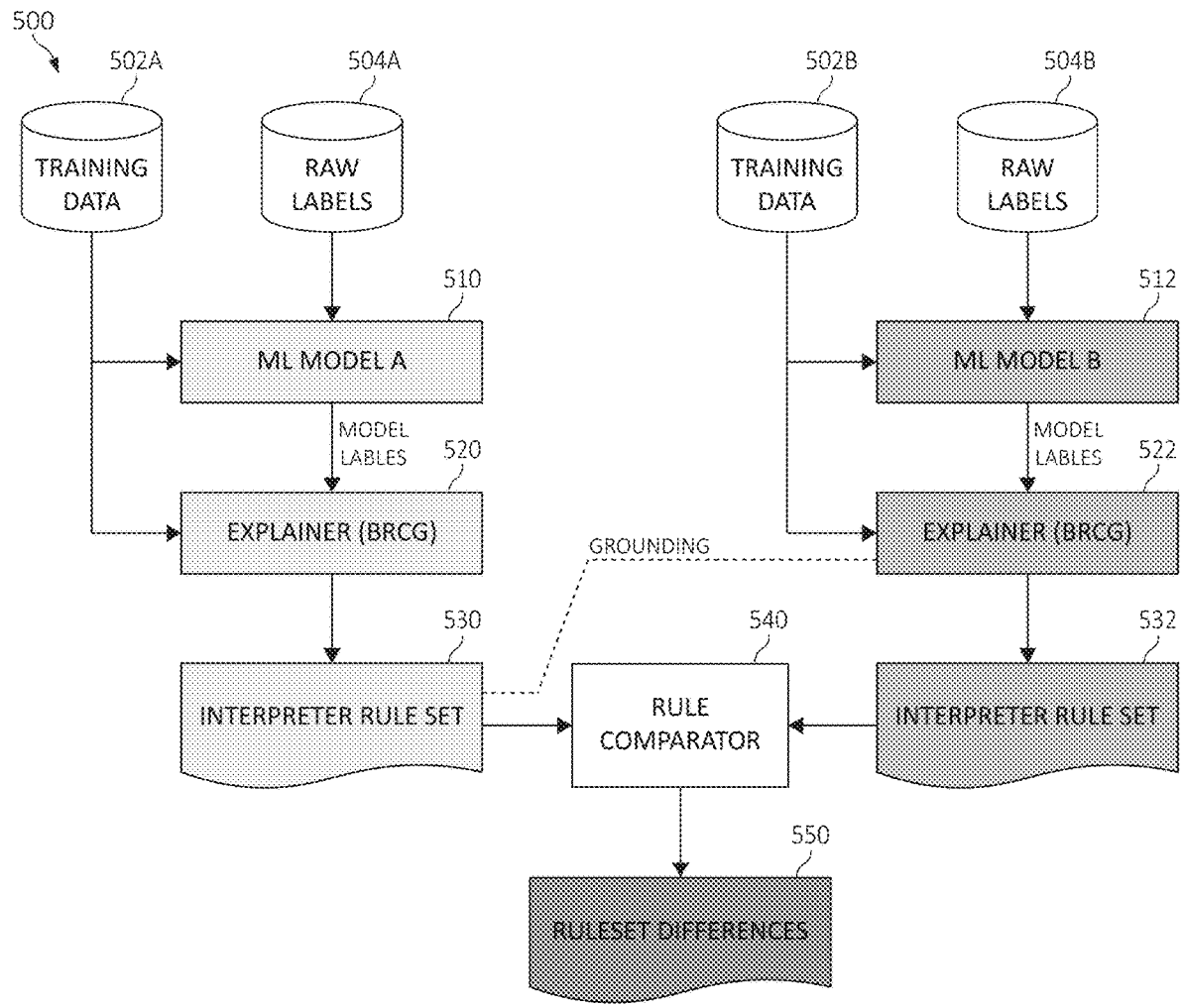
FIG. 5 depicts a block flow diagram depicting operations for providing machine learning model change management in an online Software as a Medical Device ("SaMD") in a computing environment according to an embodiment of the present invention.

Turning now to FIG. 5, block diagram depicts exemplary operations of system 500 for providing machine learning model change management in of an online Software as a Medical Device ("SaMD") in a computing environment. In one aspect, one or more of the components, modules, services, applications, and/or functions described in FIGS. 1-4 may be used in FIG. 5. As shown, various blocks of functionality are depicted with arrows designating the blocks of system 500 relationships with each other and to show process flow (e.g., steps or operations). Additionally, descriptive information is also seen relating each of the functional blocks of system 500. As will be seen, many of the functional blocks may also be considered "modules" of functionality, in the same descriptive sense as has been previously described in FIGS. 1-4. Repetitive description of like elements employed in other embodiments described herein is omitted for sake of brevity.

With the foregoing in mind, the module blocks' of systems 500 may also be incorporated into various hardware and software components of a system integrating disaggregated memory in a cloud computing environment in accordance with the present invention. Many of the functional blocks of systems 500 may execute as background processes on various components, either in distributed computing components, or elsewhere.

In operation, training data 502A, 502B and raw labels 504A and 540B may be provided as input into an online machine learning model. That is, one or more raw labels 504A and 504B, along with the training data 502A and 502B, may be input training data 502 to the machine learning model A 510 and machine learning model B 512, respectively. One or more labels (e.g., model labels) may be provided to an explainer ("BRCG") 520 and 522. In one aspect, BRCG ("Boolean Rules via Column Generation") is an explanation method and used by way of example only.

Also, the "grounding" between 520 and 522 refers to an optional operation to stabilize rules to enable the comparison (e.g., make a comparison feasible). Thus, the "grounding" operation may enhance or influences an interpretable learner with external information to achieve structural similar rules to enable comparison.

The interpretable rule set 530 and 532 may receive the data from an explainer 520 and 530, respectively, and build an interpretable rule set based on performance characteristics and compliance criteria. That is, the interpreter rule set 530 and 532 may be global rule surrogates that are built in order to provide a rule comparison. This results in an interpretable clause set that identifies sub-populations impacted by the SaMD model change. In one aspect, a "global rule surrogate" may be a set of rules (e.g., a human-readable set of rules) that describes any underlying logic of any machine learning model (e.g., a complex machine learning model). For example, assume a bank uses a complex AI/ML model to approve and/or reject mortgage applications. Without the global rule surrogate, challenges are presented on determining why the AI/ML rejects some applications while approves other applications (as the underlying model logic is not known). Thus, for example, by analysis of several AI/ML mortgage approvals/rejections, the explainer 520 may learn and build the "global rule surrogate" that learns, detects, and understands patterns of model behavior. A surrogate rule may be, for example: Rule: If age is less than 27 years of age, income is less than $25,000, then reject the mortgage application (e.g., RULE: "age<26, income<$25K) THEN (Reject").

Using the interpreter rule set 530 and 532, the rule comparator 540 may provide an interpretable model comparison to describe qualitative differences between AI/ML model versions. The rule comparator 540 may map model changes to a regulatory risk assessment framework (e.g., regulatory information and risk classification) and determine if a model change has regulatory implications. For example, the risk assessment framework may be a checklist to answer if the change has been significant. In other implementations, the risk assessment framework may be a complex version involving reporting into a machine learning process or defined process to evaluate changes.

The rule comparator 540 may also use the regulatory risk assessment frameworks (e.g., regulatory information and risk classification), the machine learning model A 510 and machine learning model B 512 specifications and associated training data 502A and 502B, and raw labels 504A and 504B, to monitor and determine acceptable change thresholds based on tracking model versions, provenance, clinical context, and performance.

The rule comparator 540 may provide one or more ruleset differences 550 based on the comparison of the current AI/ML model and a newly trained AI/ML model. That is, the ruleset differences 550 show one or more differences between the comparison of the current AI/ML model and a newly trained AI/ML model and may validate the one or more machine learning models against the interpretable rule set. The rule comparator 540 may provide an interpretable model comparison to describe qualitative differences between model versions (e.g., the current AI/ML model and a newly trained AI/ML model).

For those of the newly trained AI/ML model that are validated by the one or more machine learning models against the interpretable rule set, the rule comparator 540 may generate a certificate indicating the one or more machine learning models comply with interpretable rule set.

Figure 6:
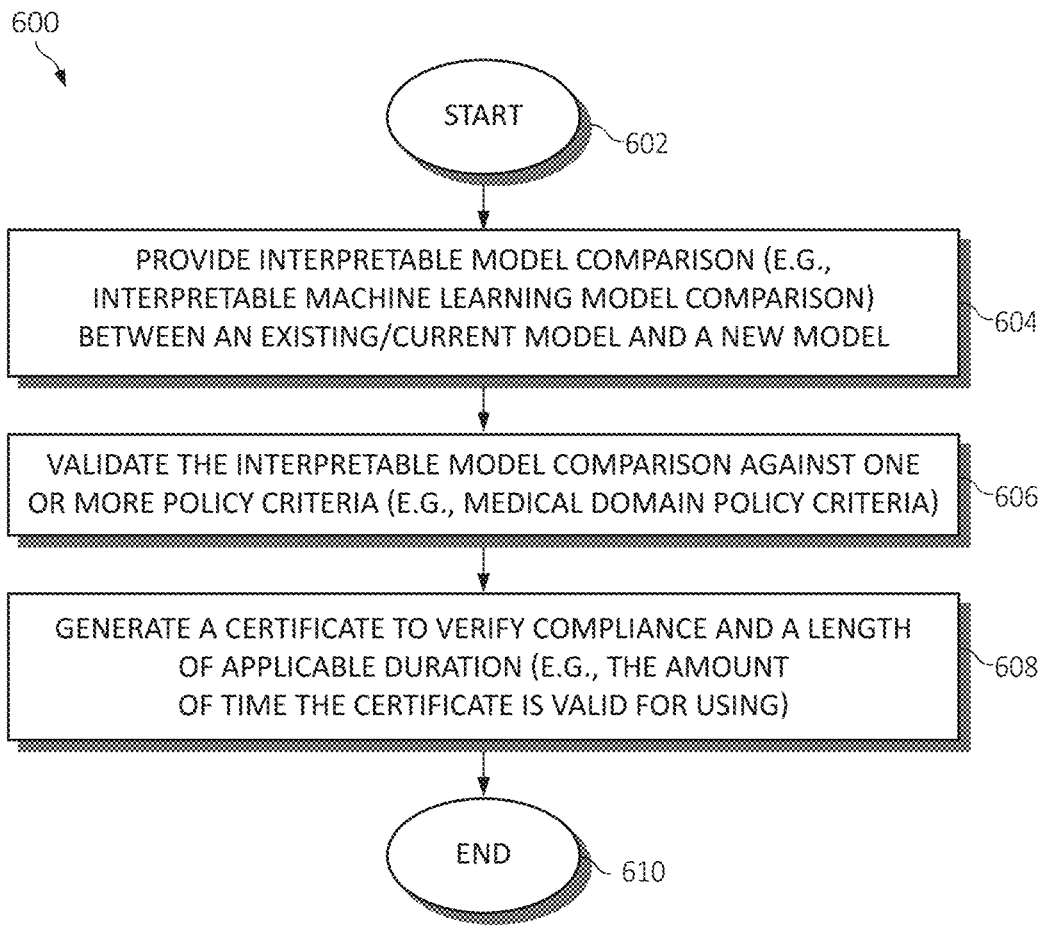
FIG. 6 is a flowchart diagram depicting an exemplary method for providing machine learning model change management in an online Software as a Medical Device ("SaMD") in a computing environment according to an embodiment of the present invention.

Turning now to FIG. 6, a method 600 for providing machine learning model change management in an online Software as a Medical Device ("SaMD") in a computing environment using a processor is depicted, in which various aspects of the illustrated embodiments may be implemented. The functionality 600 may be implemented as a method (e.g., a computer-implemented method) executed as instructions on a machine, where the instructions are included on at least one computer readable medium or one non-transitory machine-readable storage medium. The functionality 600 may start in block 602.

An interpretable model comparison (e.g., interpretable machine learning model comparison) between an existing/current model and a new model (e.g., a current machine learning model and a new machine learning model) may be provided, as in block 604. The interpretable model comparison may be validated against one or more policy criteria (e.g., medical domain policy criteria), as in block 606. A certificate to verify compliance and a length of applicable duration (e.g., the amount of time the certificate is valid for using) may be generated, as in block 608. The functionality 600 may end, as in block 610.

Figure 7:
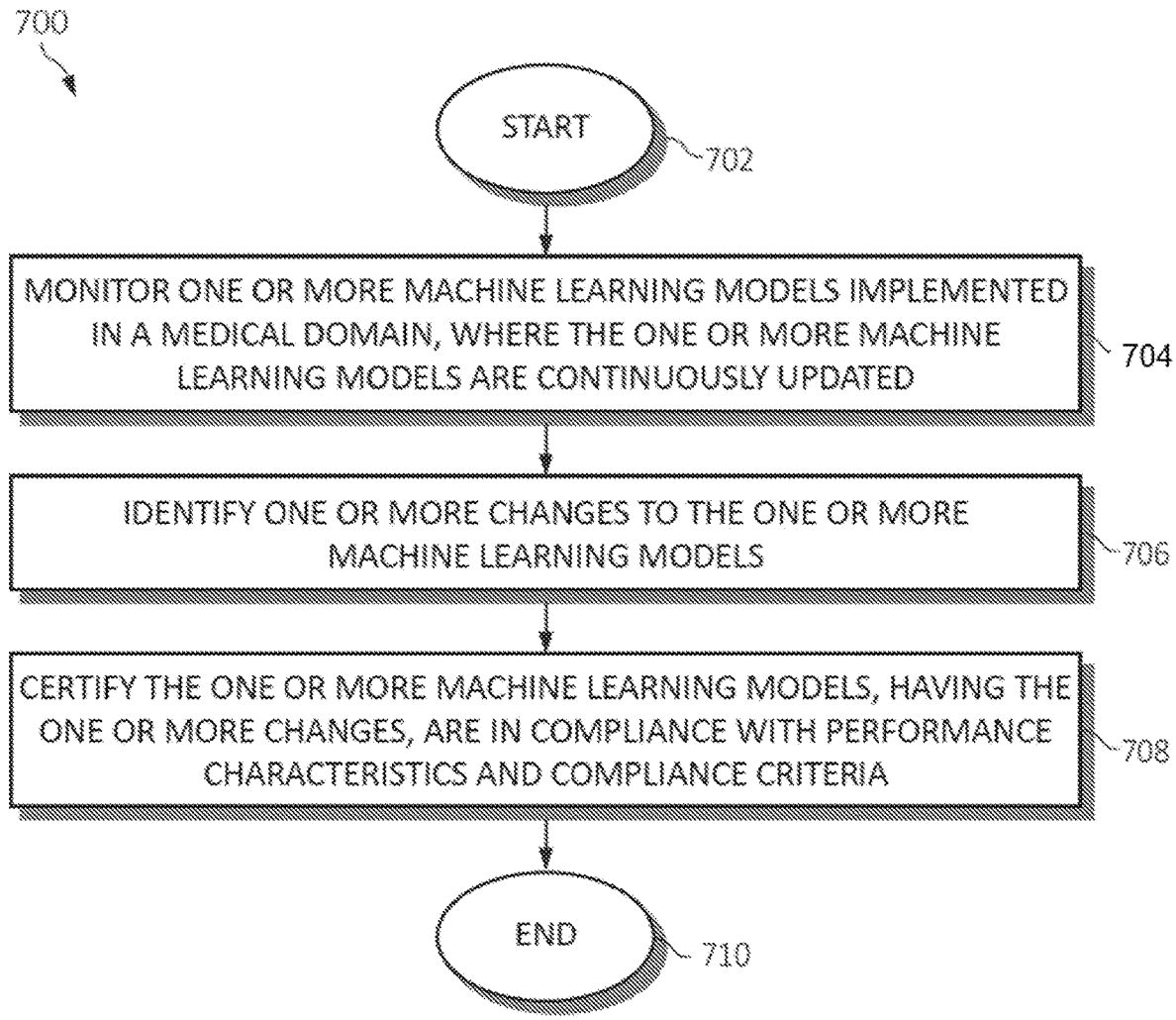
FIG. 7 is a flowchart diagram depicting an additional exemplary method for providing machine learning model change management in an online Software as a Medical Device ("SaMD") in a computing environment according to an embodiment of the present invention.

Turning now to FIG. 7, a method 700 for providing machine learning model change management in an online Software as a Medical Device ("SaMD") in a computing environment using a processor is depicted, in which various aspects of the illustrated embodiments may be implemented. The functionality 700 may be implemented as a method (e.g., a computer-implemented method) executed as instructions on a machine, where the instructions are included on at least one computer readable medium or one non-transitory machine-readable storage medium. The functionality 700 may start in block 702.

One or more machine learning models implemented in a medical domain may be monitored where the one or more machine learning models are continuously updated, as in block 704. One or more changes to the one or more machine learning models may be identified, as in block 706. The one or more machine learning models, having the one or more changes, may be certified as being in compliance with performance characteristics and compliance criteria, as in block 708. The functionality 700 may end, as in block 710.

In one aspect, in conjunction with and/or as part of at least one blocks of FIG. 7, the operations of method 700 may include each of the following. The operations of method 700 may provide an interpretable model comparison between a current more machine learning model and an updated machine learning model. The operations of method 700 may track each version of the one or more machine learning models in the medical domain.

The operations of method 700 may identify the one or more changes compromise the performance characteristics and compliance criteria of the one or more machine learning models. The operations of method 700 may update and retain the one or more machine learning models to achieve compliance with the performance characteristics and compliance criteria.

The operations of method 700 may map the one or more changes of the one or more machine learning models to a risk assessment domain. The operations of method 700 may build an interpretable rule set based on performance characteristics and compliance criteria; validate the one or more machine learning models against the interpretable rule set; and generate a certificate indicating the one or more machine learning models comply with interpretable rule set.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The descriptions of the embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
    monitoring, by one or more processors, an online machine learning model that utilizes a Bayesian network implemented in a medical device, wherein the online machine learning model dynamically learns, retrains, and adapts based on new data;
    determining, by one or more processors, that a change to the online machine learning model results in the online machine learning model implemented in the medical device requiring recertification, wherein the online machine learning model uses sensor-based devices that include audio and video devices, the determining comprising:
        performing, by one or more processors, a grounding operation between different model versions corresponding to the change to the online machine learning model, wherein the grounding operation influences an interpretable learning with external information until achieving structurally similar rules for comparison;
        mapping, by one or more processors, model changes to a regulatory risk assessment framework, wherein the regulatory risk assessment framework requires reporting into a machine learning process to evaluate change thresholds based on tracking model versions, provenance, clinical context, and performance; and
    presenting, by one or more processors, a user-interpretable summary of the change to the online machine learning model; and
    responsive to determining that the change to the online machine learning model implemented in the medical device results in the online machine learning model implemented in the medical device requiring recertification, generating, by one or more processors, a certificate, the certificate:
        indicating that the online machine learning model implemented in the medical device having the change is in compliance with performance characteristics and compliance criteria; and
        specifying a duration of time the certificate remains valid.

2. The computer-implemented method of claim 1, further comprising tracking, by one or more processors, each version of the online machine learning model implemented in the medical device.

3. The computer-implemented method of claim 1, further comprising identifying, by one or more processors, the change comprises the performance characteristics and compliance criteria of the online machine learning model.

4. The computer-implemented method of claim 1, further comprising updating and retraining, by one or more processors, the online machine learning model to achieve compliance with the performance characteristics and compliance criteria.

5. The computer-implemented method of claim 1, further comprising:
    building, by one or more processors, an interpretable rule set based on performance characteristics and compliance criteria;
    validating, by one or more processors, the online machine learning model against the interpretable rule set; and
    wherein the certificate indicates that the online machine learning model complies with the interpretable rule set.

6. The computer-implemented method of claim 1, wherein the change is selected from the group consisting of new data signals in the online machine learning model that impact analytical performance and scope of use change.

7. The computer-implemented method of claim 1, wherein the online machine learning model implemented in the medical domain is Software as a Medical Device (SaMD), wherein SaMD collects, processes, diagnoses, and analyzes healthcare data.

8. The computer-implemented method of claim 1, wherein the performance characteristics comprise clinical and analytical performance characteristics, the analytical performance comprising a specificity of method in detecting abnormal tissue in a scan.

9. A computer system comprising:
   a processor set;
   a set of one or more computer-readable storage media storing program instructions executable by the processor set;
   program instructions to monitor an online machine learning model that utilizes a Bayesian network implemented in a medical device, wherein the online machine learning model dynamically learns, retrains, and adapts based on new data;
   program instructions to determine that a change to the online machine learning model results in the online machine learning model implemented in the medical device requiring recertification, wherein the online machine learning model uses sensor-based devices that include audio and video devices, the determining comprising:
      performing a grounding operation between different model versions corresponding to the change to the online machine learning model, wherein the grounding operation influences an interpretable learning with external information until achieving structurally similar rules for comparison;
      mapping model changes to a regulatory risk assessment framework, wherein the regulatory risk assessment framework requires reporting into a machine learning process to evaluate change thresholds based on tracking model versions, provenance, clinical context, and performance; and
      presenting a user-interpretable summary of the change to the online machine learning model; and
   program instructions, responsive to determining that the change to the online machine learning model implemented in the medical device results in the online machine learning model implemented in the medical device requiring recertification, to generate a certificate, the certificate:
      indicating that the online machine learning model implemented in the medical device having the change is in compliance with performance characteristics and compliance criteria; and
      specifying a duration of time the certificate remains valid.

10. The computer system of claim 9, further comprising program instructions to track each version of the online machine learning model implemented in the medical device.

11. The computer system of claim 9, further comprising program instructions to identify the change comprising the performance characteristics and compliance criteria of the online machine learning model.

12. The computer system of claim 9, further comprising program instructions to update and retrain the online machine learning model to achieve compliance with the performance characteristics and compliance criteria.

13. The computer system of claim 9, further comprising:
   program instructions to build an interpretable rule set based on performance characteristics and compliance criteria;
   program instructions to validate the online machine learning model against the interpretable rule set; and
   wherein the certificate indicates that the online machine learning model complies with the interpretable rule set.

14. A computer program product comprising:
   a set of one or more computer readable storage media storing program instructions executable by a processor set;
   program instructions to monitor an online machine learning model that utilizes a Bayesian network implemented in a medical device, wherein the online machine learning model dynamically learns, retrains, and adapts based on new data;
   program instructions to determine that a change to the online machine learning model results in the online machine learning model implemented in the medical device requiring recertification, wherein the online machine learning model uses sensor-based devices that include audio and video devices, the determining comprising:
      performing a grounding operation between different model versions corresponding to the change to the online machine learning model, wherein the grounding operation influences an interpretable learning with external information until achieving structurally similar rules for comparison;
      mapping model changes to a regulatory risk assessment framework, wherein the regulatory risk assessment framework requires reporting into a machine learning process to evaluate change thresholds based on tracking model versions, provenance, clinical context, and performance; and
      presenting a user-interpretable summary of the change to the online machine learning model; and
   program instructions, responsive to determining that the change to the online machine learning model implemented in the medical device results in the online machine learning model implemented in the medical device requiring recertification, to generate a certificate, the certificate:
      indicating that the online machine learning model implemented in the medical device having the change is in compliance with performance characteristics and compliance criteria; and
      specifying a duration of time the certificate remains valid.

15. The computer program product of claim 14, further comprising:
   program instructions to track each version of the online machine learning model implemented in the medical device; and
   program instructions to identify the change comprising the performance characteristics and compliance criteria of the online machine learning model.

16. The computer program product of claim 14, further comprising program instructions to update and retrain the machine learning model to achieve compliance with the performance characteristics and compliance criteria.

17. The computer program product of claim 14, further comprising:

program instructions to build an interpretable rule set based on performance characteristics and compliance criteria;
program instructions to validate the online machine learning model against the interpretable rule set; and
wherein the certificate indicates that the online machine learning model complies with the interpretable rule set.

* * * * *